United States Patent [19]
Moore et al.

[11] Patent Number: 5,502,094
[45] Date of Patent: Mar. 26, 1996

[54] PHYSIOLOGICALLY ACCEPTABLE EMULSIONS CONTAINING PERFLUOROCARBON ETHER HYDRIDES AND METHODS FOR USE

[75] Inventors: George G. I. Moore, Afton; Richard M. Flynn, Mahtomedi; Miguel A. Guerra, Woodbury, all of Minn.

[73] Assignee: Minnesota Mining and Manufacturing Company, Saint Paul, Minn.

[21] Appl. No.: 437,299

[22] Filed: May 17, 1995

Related U.S. Application Data

[63] Continuation-in-part of Ser. No. 246,962, May 20, 1994.
[51] Int. Cl.⁶ ......................................................... C08K 5/52
[52] U.S. Cl. ........................... 524/145; 514/832; 514/937; 514/941; 524/77; 524/81; 524/145; 524/220; 524/801; 524/805
[58] Field of Search ...................................... 514/937, 941, 514/832; 524/77, 81, 145, 220, 801, 805

[56] References Cited

U.S. PATENT DOCUMENTS

| | | | |
|---|---|---|---|
| 3,493,581 | 2/1970 | Heinrick et al. | |
| 3,911,138 | 10/1975 | Clark, Jr. | 424/352 |
| 3,962,439 | 6/1976 | Yokoyama et al. | 424/248 |
| 4,110,474 | 8/1978 | Lagow et al. | 424/350 |
| 4,186,253 | 1/1980 | Yokoyama et al. | 435/240 |
| 4,187,252 | 4/1980 | Lagow et al. | 260/653 |
| 4,252,827 | 2/1981 | Yokoyama et al. | 424/366 |
| 4,423,077 | 12/1983 | Sloviter | 424/325 |
| 4,443,480 | 4/1984 | Clark, Jr. | 424/352 |
| 4,534,978 | 8/1985 | Yokoyama | 514/429 |
| 4,686,024 | 8/1987 | Scherer, Jr. | 204/157.95 |
| 4,865,836 | 9/1989 | Long, Jr. | 424/5 |
| 4,866,096 | 9/1989 | Schweighardt | 514/756 |
| 4,868,318 | 9/1989 | Scherer, Jr. et al. | 549/362 |

FOREIGN PATENT DOCUMENTS

| | | |
|---|---|---|
| 158996 | 10/1985 | European Pat. Off. |
| 231091 | 8/1987 | European Pat. Off. |
| 2650586 | 5/1977 | Germany |
| 1549038 | 7/1979 | United Kingdom |
| 89/10118 | 11/1989 | WIPO |

OTHER PUBLICATIONS

L. C. Clark, Jr., et al., "Emulsions of perfluorinated solvents for intravascular gas transport" *Fed. Proc.*, 34(6), pp. 1468–1477 (1975).

K. Yokoyama, et al., "A Perfluorochemical Emulsion as an Oxygen Carrier" *Artif. Organs*, 8(1), pp. 34–40 (1984).

K. Yamanouchi, et al., "Quantitative Structure–in vivo Half–Life Relationships of Perfluorochemicals for Use as Oxygen Transporters" *Chem, Pharm. Bull.*, 33(3), pp. 1221–1231 (1985).

J. G. Reiss, et al., "Design, Synthesis & Evaluation of Fluorocarbons & Surfactants for in vivo Applications New Perfluoroalkylated Polyhydroxylated Surfactants" *Artif. Cells Artif. Organs*, 16 (1–3), pp. 421–430 (1988).

T. Kawamura, et al., "A New Simple Two Layer (Euro–Collins' Solution/Perfluorochemical) Cold Storage Method for Pancreas Preservation" *Transplantation Proc.*, 21(1), pp. 1376–1377 (1989).

L. D. Segel, et al., "Albumin improves stability and longevity of perfluorochemical–perfused hearts" *Am. J. Physiol.*, 254, pp. H1105–H1112 (1988).

L. D. Segel, et al., "Prolonged support of working rabbit hearts using Fluosol–43 or erythrocyte media" *Am. J. Physiol.*, 252, pp. H349–H359 (1987).

L. D. Segel, et al., "Isolated working rat heart perfusion with perfluorochemical emulsion Fluosol–43" *Am. J. Physiol.*, 242, pp. H485–H489 (1982).

B. A. Teicher, et al., "Oxygen–carrying Perfluorochemical Emulsion as an Adjuvant Radiation Therapy in Mice" *Cancer Res.*, 44, pp. 4285–4288 (1984).

B. A. Teicher, et al., "Effects of Dose and Scheduling on Growth Delay of the Lewis Lung Carcinoma Produced by the Perfluorochemical Emulsion", Fluosol–DA$^R$ *Int. J. Radiation Oncology Biol. Phys.*, 12, pp. 1311–1313 (1986).

S. Rockwell, et al., "Reactions of Tumors and Normal Tissues in Mice to Irradiation in the Presence and Absence of a Perfluorochemical Emulsion" *Int. J. Radiation Oncology Biol. Phys.*, 12, pp. 1315–1318 (1986).

B. A. Teicher, et al., "Perfluorochemical Emulsions Can Increase Tumor Radiosensitivity" *Science*, 223, pp. 934–936 (1984).

B. A. Teicher, et al., "Effect of Various Oxygenation Conditions & Fluosol–DA on Cytotoxicity and Antitumor Activity in Bleomycin in Mice" *J. Natl. Cancer Inst.*, 80, pp. 599–603 (1988).

R. Virmani, et al., "Myocardial protection by perfluorochemical infusion during transient ichemia produced by balloon coronary occlusion" *Am. Heart J.*, 116, pp. 421–431 (1988).

C. C. Jaffe, et al., "Preservation of left ventricular ejection fraction during percutaneous transluminal coronary angioplasty by distal transcatheter coronary perfusion of oxygenated Fluosol DA 20%" *Am. Heart J.*, 115, pp. 1156–1164 (1988).

M. Clemen, et al., "Prevention of ischemia during percutaneous transluminal coronary angioplasty by transcatheter infusion of oxygenated Fluosol DA 20%" *Circulation*, 74, pp. 555–562 (1986).

(List continued on next page.)

*Primary Examiner*—Samuel A. Acquah
*Attorney, Agent, or Firm*—Wood, Herron & Evans

[57] ABSTRACT

This invention relates to physiologically acceptable emulsions of perfluorocarbon ether hydrides having 8 to 12 carbon atoms. These novel emulsions have various medical applications. They are especially useful medically as contrast media for various biological imaging modalities such as nuclear magnetic resonance, ¹⁹F-magnetic resonance imaging, ultrasound, x-ray, and computed tomography, as oxygen transport agents or "artificial bloods" in the treatment of heart attack, stroke, and other vascular obstructions, as adjuvants to coronary angioplasty and in cancer radiation treatment and chemotherapy.

19 Claims, No Drawings

OTHER PUBLICATIONS

H. V. Anderson, et al., "Distal coronary artery perfusion during percutaneous transluminal coronary angioplasty" *Am. Heart J.*, 110, pp. 720–726 (1984).

S. J. Peerless, et al., "Modification of Cerebral Ischemia With Fluosol" *Stroke*, 16, pp. 38–43 (1985).

J. L. Osterholm, et al., "Severe Cerebral Ischemia Treatment by Ventriculosubarachnoid Perfusion with an Oxygenated Fluorocarbon Emulsion" *Neurosurg.*, 13, pp. 381–387 (1983).

S. J. Peerless, et al., "Protective Effect of Fluosol–DA in Acute Cerebral Ischemia" *Stroke*, 12, pp. 558–563 (1981).

M. B. Forman, et al., "Reduction of infarct size with intracoronary perfluorochemical in a canine prepartion of reperfusion" *Circulation*, 71, pp. 1060–1068 (1985).

PHYSIOLOGICALLY ACCEPTABLE EMULSIONS CONTAINING PERFLUOROCARBON ETHER HYDRIDES AND METHODS FOR USE

RELATED APPLICATION

This application is a continuation-in-part application of application Ser. No. 08/246,962 filed May 20, 1994, entitled OMEGA-HYDROFLUOROALKYL ETHERS, PRECURSOR CARBOXYLIC ACIDS AND DERIVATIVES THEREOF, AND THEIR PREPARATION AND APPLICATION in the names of George G. I. Moore, Richard M. Flynn, Miguel A. Guerra and John G. Owens. The specification and claims of that entire application are incorporated herein by reference.

TECHNICAL FIELD OF INVENTION

This invention relates to physiologically acceptable aqueous emulsions of perfluorocarbon ether hydrides having 8 to 12 carbon atoms. The novel emulsions have various medical applications. They are especially useful medically as contrast media for various biological imaging modalities, such as nuclear magnetic resonance, $^{19}$F-magnetic resonance imaging, ultrasound, x-ray, and computed tomography, as oxygen transport agents or "artificial bloods" in the treatment of heart attack, stroke, and other vascular obstructions, as adjuvants to coronary angioplasty and in cancer radiation treatment and chemotherapy.

BACKGROUND OF THE INVENTION

Highly fluorinated organic compounds, and particularly perfluorocarbon compounds, are well known to be both stable and chemically inert. During the past 25 years much attention has focused on the use of such compounds in biological systems because they are capable of dissolving and transporting large amounts of oxygen. These properties make them potentially useful as contrast media, oxygen transport agents or "artificial bloods" in the treatment of heart attack, stroke, and other vascular obstructions, as adjuvants to coronary angioplasty, and in cancer radiation treatment and chemotherapy.

Among the highly fluorinated organic compounds that are said to be useful in such applications are perfluorocarbon compounds, e.g., perfluorodecalin, perfluoroindane, perfluorotrimethyl bicyclo [3.3.1] nonane, perfluoromethyl adamantane, perfluorodimethyl adamantane, and perfluoro-2,2,4,4-tetramethylpentane; 9–12C perfluoro amines, e.g., perfluorotripropyl amine, perfluorotributyl amine, perfluoro-1-azatricyclic amines; bromofluorocarbon compounds, e.g., perfluorooctyl bromide and perfluorooctyl dibromide; F-4-methyl octahydroquinolidizine and perfluoro ethers, including chlorinated polyfluorocyclic ethers. Such compounds are described, for example, in U.S. Pat. Nos. 3,962,439, 3,493,581, 4,110,474, 4,186,253, 4,187,252, 4,252,827, 4,423,077, 4,443,480, 4,534,978, 4,686,024, 4,865,836, 4,866,096 and 4,868,318, European patent applications 80710 and 158,996, British patent specification 1,549,038 and German Offen. 2,650,586.

For intravenous use, highly fluorinated organic compounds must be dispersed as emulsions. See, e.g., L. C. Clark, Jr. et al., "Emulsions Of Perfluorinated Solvents For Intravascular Gas Transport," *Fed. Proc.*, 34(6), pp. 1468–77 (1975); K. Yokoyama et al., "A Perfluorochemical Emulsion As An Oxygen Carrier," *Artif. Organs (Cleve)*, 8(1), pp 34–40 (1984); and U.S. Pat. Nos. 4,110,474 and 4,187,252. Neat, highly fluorinated organic compounds are immiscible in blood.

U.S. Pat. No. 3,991,138 discloses perfluorocarbon emulsions as artificial bloods having fluorocarbons that may be excreted from the animal body within a clinically acceptable time period. In the '138 patent, for example, perfluorocyclocarbons were found to leave the animal body at a faster rate than other perfluorocarbons. In contrast, when perfluorocarbon ethers were administered to an animal, they were found to reside in the liver and spleen rather indefinitely. More recently, a hydrofluoroalkyl ether, F[CF(CF$_3$)CF$_2$O]$_4$CFHCF$_3$, has been tested as a synthetic blood emulsion, but it also tends to stay in the body, see *Chem. Pharm. Bull.*, 33, 1221 (1985). In general, the perfluorocarbon ethers have been regarded as unsatisfactory candidates for use as oxygen transport agents and for medical purposes because they tend to reside rather indefinitely in the animal body.

In view of the above background, the search continues for emulsions containing perfluorocarbons that function effectively as oxygen transport agents and that may be excreted from the body within a clinically acceptable time period. Such emulsions must not only contain a high enough concentration of the highly fluorinated organic compound to be effective at the desired level of oxygen transport, they must also be capable of sterilization, preferably by heat, have long term stability in the fluid or non-frozen state, persist for sufficiently long times in the blood stream to deliver useful quantities of oxygen and yet be eliminated rapidly enough from the body to avoid toxicity and retention in body parts and organs.

SUMMARY OF THE INVENTION

This invention relates to physiologically acceptable aqueous emulsions of perfluorocarbon ether hydrides, particularly hydroperfluoroaliphatic ethers or such ethers substituted with a perfluoroalicyclic group ("PFC ether hydride(s)"). It has been discovered that these PFC ether hydrides function very effectively as oxygen transport agents, yet they have very surprisingly short residence times in the animal body. In fact, these PFC ether hydrides have been found to persist for a sufficient time in the bloodstream to deliver useful quantities of oxygen and yet be eliminated rapidly from the body so that no trace in essential organs is observable even within several days after administration. These remarkable PFC ether hydrides are excellent candidates for use in artificial blood and oxygen transport emulsions.

The emulsions of this invention are useful in various medical applications, e.g., as contrast media for various biological imaging modalities, including nuclear magnetic resonance, $^{19}$F-magnetic resonance imaging, ultrasound, x-ray, and computed tomography, as oxygen transport agents or "artificial bloods" in the treatment of heart attack, stroke, and other vascular obstructions, as adjuvants to coronary angioplasty and in cancer radiation and chemotherapy.

More particularly, the physiologically acceptable emulsions of this invention contain a C$_8$ to C$_{12}$ saturated hydroperfluoroaliphatic ether or such an ether substituted with a perfluoroalicyclic group, or mixtures thereof. The aliphatic ether is a straight-chain or branched-chain of carbon atoms. The other components of the emulsion include water and a surfactant, where the components are contained in the emulsions in amounts for acceptable physiological administration.

Especially preferred emulsions contain C$_9$ to C$_{11}$ PFC ether hydrides which have been found to reside for an extremely short time in the essential organs such as the liver.

The PFC ether hydrides offer a new dimension of synthetic flexibility in the formulation of physiologically acceptable emulsions. These PFC ether hydrides may be easily made and have lower densities and boiling points which render them very suitable for administration, oxygen transport and excretion from the animal body. These PFC ether hydrides also have no adverse effects upon the lungs upon clearing the body. Their volatility, molecular weight, solubility and ozone friendly characteristics make them leading candidates in medical applications. The invention, its advantages and further embodiments will be further understood with reference to the following detailed description and operating examples.

DETAILED DESCRIPTION OF THE INVENTION

In this description, the term "perfluoro", such as is the case of "perfluoroaliphatic", "perfluoroalicyclic", "perfluoroalkyl", or "perfluoroalkylene", means that except as may be otherwise indicated by the prefix "hydro", there are neither any carbon-bonded hydrogen atoms replaceable with fluorine, nor any unsaturation. Thus, the term "hydroperfluoroaliphatic ether" means there is at least one carbon-bonded hydrogen atom and the remainder of carbon atoms in the aliphatic group are bonded to fluorine or oxygen in the compound. This compound may also be called "perfluoroaliphatic ether hydride". The prefixes "dihydro" and "trihydro" mean there are respectively two or three carbon-bonded hydrogen atoms in the compound. For simplicity, sometimes hereinafter "PFC ether hydride" is meant to include all forms of compounds suitable for use in this invention whether they contain one to three hydrogen atoms, one or more ether-oxygen atoms, or the carbon group is aliphatic, alicyclic or alicyclic-substituted aliphatic, either straight-chain or branched-chain. Also, "1° hydrogen" or "2° hydrogen" herinafter means the hydrogen atom is bonded to a primary or a secondary carbon atom, respectively.

The physiologically acceptable aqueous emulsions of this invention contain a $C_8$–$C_{12}$ PFC ether hydride, water and a surfactant, where the components are contained in the emulsion in amounts for acceptable physiological administration. The PFC ether hydride is selected from the group of a saturated $C_8$ to $C_{12}$ hydroperfluoroaliphatic ether, a hydroperfluoroaliphatic ether substituted with a saturated perfluoroalicyclic group, and a hydroperfluorocycloaliphatic ether and mixtures of such ethers. These aliphatic ethers have either straight-chain or branched-chain carbon atoms. By "saturated", it is meant that these compounds have no double bonds or unsaturation in the molecule.

In a presently preferred form, the emulsions contain a $C_9$–$C_{11}$ PFC ether hydride because these compounds have been found to most effectively perform as oxygen transport agents in the emulsions and only temporarily reside in the body. As a class, the PFC ether hydrides have boiling points of at least about 120° C. which render them nontoxic with satisfactory clearance rates from the animal body.

A preferred class of PFC ether hydrides may be represented by the Formula I:

X-R$_f$-O(R$_f'$-O)$_n$R$_f''$-H wherein:
H is a primary hydrogen atom or a 2°·hydrogen atom on a carbon adjacent to an ether oxygen atom;
X is a fluorine atom, a primary hydrogen atom, or a 2° hydrogen atom on a carbon adjacent to an ether oxygen atom;
n is an integer of 0 to 4; and
R$_f$, R$_f'$ and R$_f''$ are independently selected from unbranched or branched groups consisting of perfluoroalkylene, perfluorocycloalkylene, or perfluorocycloalkylene containing one or more ether oxygens. Compounds of Formula I in which hydrogen atoms are either primary or secondary and attached to a carbon adjacent to an ether oxygen are preferred because they are easy to prepare and more stable to exposure to base, heat, and oxidative conditions. Therefore, they are more likely to withstand heat sterilization and less likely to be biologically reactive or metabolized.

A first group of PFC ether hydrides within Formula I which are especially preferred are $C_9$–$C_{10}$ dihydroperfluorocarbon ethers in which the hydrogen atoms may be 1°, or 2° on a carbon atom adjacent to an ether oxygen. These may be represented by the following compounds which leave the body either within several days or a very short time. Hereinafter the "cyclo-$C_6F_{11}$–" or "cyclo-$C_6F_{10}$–" represents the perfluorocyclohexyl group or perfluorocyclohexylene respectively.

H-C$_3$F$_6$OC$_4$F$_8$OC$_3$F$_6$-H
H-C$_2$F$_4$OCF$_2$C(CF$_3$)$_2$CF$_2$OC$_2$F$_4$-H
H-C$_2$F$_4$-O-(CF$_2$)$_5$-O-C$_2$F$_4$-H
H-C$_2$F$_4$-O-(CF$_2$)$_6$-O-C$_2$F$_4$-H
H-CF$_2$O-(C$_2$F$_4$O)$_3$CF$_2$-H
H-CF$_2$O-(C$_2$F$_4$O)$_4$CF$_2$-H
H-C$_2$F$_4$-O-cyclo-C$_6$F$_{10}$-O-C$_2$F$_4$-H A second group of preferred PFC ether hydrides within the scope of Formula I are $C_9$–$C_{11}$ perfluorocycloalkyl- or perfluorocycloalkyl-substituted perfluoroalkylene ether hydrides, as represented by the following compounds which leave the body within several days:

cyclo-C$_6$F$_{11}$—CF$_2$OC$_2$F$_4$H
cyclo-C$_6$F$_{11}$—OC$_4$F$_8$H
cyclo-C$_6$F$_{11}$—C$_2$F$_4$OCF$_2$—H
p-CF$_3$O-cyclo-C$_6$F$_{10}$—C$_2$F$_4$—H

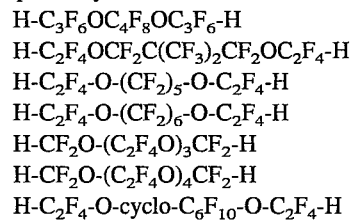

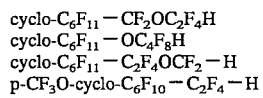

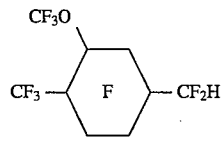

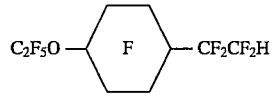

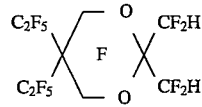

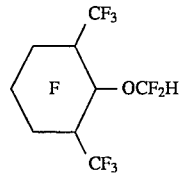

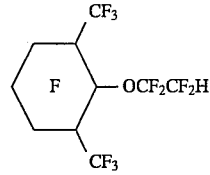

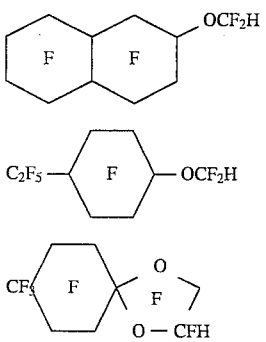

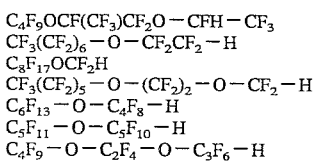

A third class of hydroperfluoroalkyl ethers that are preferred include $C_9$–$C_{10}$ hydroperfluoroalkyl ethers where the hydrogen atom is 1° or is 2° bonded to a carbon atom adjacent to an ether oxygen either bonded to an end carbon or intermediate carbon adjacent to an ether as represented by the following compounds:

$C_4F_9OCF(CF_3)CF_2O$—$CFH$—$CF_3$
$CF_3(CF_2)_6$—$O$—$CF_2CF_2$—$H$
$C_8F_{17}OCF_2H$
$CF_3(CF_2)_5$—$O$—$(CF_2)_2$—$O$—$CF_2$—$H$
$C_6F_{13}$—$O$—$C_4F_8$—$H$
$C_5F_{11}$—$O$—$C_5F_{10}$—$H$
$C_4F_9$—$O$—$C_2F_4$—$O$—$C_3F_6$—$H$

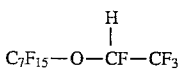

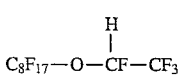

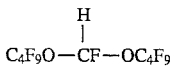

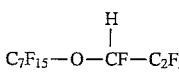

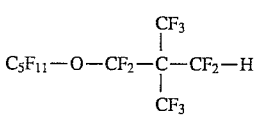

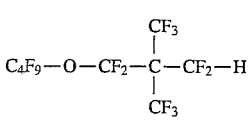

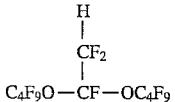

$CF_3O$—$C_8F_{16}$—$CF_2H$
$C_9F_{19}$—$O$—$CF_2$—$H$

The PFC ether hydrides of this invention typically contain one to five ether oxygen atoms. Preferably, one or two ether oxygens are present in the monohydrides and up to 5 ether oxygens are present in the dihydrides. Although the hydrogen atom can in principle be located on any carbon in the compound, we prefer, when there is more than one such hydrogen, that they be on different carbons (i.e., not geminal). In one most preferred form of the PFC ether hydride of this invention, a hydrogen is located at opposite ends of the carbon chain. Thus, they are sometimes referred to herein as "diomegahydro" perfluoroalkyl ethers.

It should be understood that any of the PFC ether hydrides of this invention may be mixed together or with other well known highly fluorinated organic compounds and used in the emulsions of this invention. For intravenous use, such emulsions may comprise 10% up to about 75% (by volume) of the PFC ether hydride. Preferably, the emulsions of this invention comprise from about 10% to about 50% (by volume) of the PFC ether hydride, and, most preferably, at least about 40% (by volume).

When the emulsions are to be used as "artificial bloods" or red blood cell substitutes, the PFC is present in as high a volume concentration as possible, e.g., 40% by volume is often preferred because that concentration matches the approximate oxygen content capacity of whole blood.

The emulsions of this invention are made using conventional means and methods and include components common to the well known emulsions of highly fluorinated organic compounds. Among the surfactants useful in the emulsions of this invention are any of the known anionic, cationic, nonionic and zwitterionic surfactants. Preferred are the nonionic surfactants, such as alkyl or aryl compounds, whose hydrophilic part consists of polyoxyethylene chains, sugar molecules, polyalcohol derivatives or other hydrophilic groups, for example, any of the BASF Wyandotte formulations of polyoxyethylene and polyoxypropylene oxides sold under the tradename "Pluronic", for example, Pluronic F-68 or F-108, or zwitterionic surfactants. Fluorinated surfactants, e.g., ATSURF® F-31 (ICI, Wilmington, Del.), may also be used in the emulsions of this invention. See, e.g., Riess et al., "Design, Synthesis And Evaluation Of Fluorocarbons And Surfactants For In Vivo Applications, New Perfluoroalkylated Polyhydroxylated Surfactants", *Artif. Cells Artif. Organs,* 16, pp. 421–30 (1988). Again, combinations of these surfactants may, of course, be used in the emulsions of this invention. In addition, mixtures of compounds, one or more of which are not surfactants, but which compounds when combined act as surfactants, may also be usefully employed as the surfactant component of the emulsions of this invention.

While the compositions may be generally referred to herein as emulsions, it should be understood that they may be considered solutions, miceliar solutions, microemulsions, vesicular suspensions, or mixtures of all of these physical states. Accordingly, the term "emulsion" as used herein covers all these states and the novel surfactant or solubilizing agent is employed to enhance stable mixtures of these states and the novel surfactant or solubilizing agent is employed to enhance stable mixtures of these physical states of the oil and water phases.

The surfactants used in the emulsions of this invention are physiologically acceptable, for example, preferably one or more of the following: egg and soybean phosphatides, lecithin, and alkyl salts of oleic acid, such as sodium oleate. Most preferable is lecithin. While the amount of a particular surfactant used in the emulsions of this invention depends on the amounts and properties of the other components of the emulsion, typically we employ between about 0.5 and 10% (by weight of the total emulsion) of surfactant. More preferably, we use about 1 to about 4% (by weight).

The emulsions of this invention may also contain an oil that is not substantially surface active and not significantly water soluble. Such oils are, for example, described in EP 231,091, WO 89/10118 and U.S. Pat. No. 4,866,096. They include liquid fatty oils, hydrocarbons, waxes, such as monoesters of a fatty acid and a monohydroxide alcohol, long chain ethers, diglycerides, triglycerides, silicone oils and nitriles. Among the useful oils in these classes are palmitoyl oleate, octyl nitrile, dodecyl nitrile, soybean oil, safflower oil, mineral oil, hexadecane, and diglycerides and triglycerides having a $C_{12-18}$ carbon chain. Of course, any mixture of triglycerides and or oils that are similar in fatty acid composition to triglycerides may be used. These oils may be used singly or in various combinations in the emulsions and processes of this invention. When our emulsions are to be used medically, the oil or combination of oils must, of course, be physiologically acceptable liquid fatty oils, such as soybean and safflower oils.

The amount of oil, or oils, if present, in the emulsions of this invention may vary over a wide range of concentrations depending on the concentration and properties of the other components of the emulsion, being principally dependent on the characteristics of the PFC ether hydride of the emulsion. The actual oil concentration to produce an acceptable emulsion for any given set of components is easily determined as taught by this invention using the simple techniques of preparing the emulsions at various oil concentrations. Within this teaching, we typically employ between about 0.5 and 20 v/v% of oil or a mixture of oils. Preferably, we employ between about 1 and 5 v/v%.

In addition to the perfluoroalkyl ether hydrides, oils, surfactants and water, the emulsions of this invention may also contain other components conventionally used in "artificial bloods" or blood substitutes, oxygen transport agents or contrast media. For example, emulsions according to this invention usually also contain an isotonic agent, typically sugars, such as glucose, mannose and fructose, glycerin, or other polyhydric alcohols to adjust the osmotic pressure of the emulsion to about that of blood. Osmolarity may also be adjusted after sterilization by buffers such as sodium chloride, sodium bicarbonate, magnesium chloride, and the like, to reduce the possibility of red blood cell injury. For example, we typically use between about 1 and 2.5% (by weight of the emulsion) of such agents. However, other amounts and other osmotic pressure controlling agents, e.g., Tyrode solution, could as well be used. In addition, these emulsions may be mixed with 0.9% saline, lactated Ringer's solution, and serum and serum products with no adverse effect on emulsion particle size and stability. The emulsions of this invention may also include other components, such as osmotic agents, e.g., dextran or hydroxyethylostarch (HES), and antioxidants.

In the most preferred emulsions of this invention, the PFC ether hydride is $C_9$–$C_{10}$, the surfactant is egg yolk lecithin, and the oil, if present, is safflower oil. Glycerin is typically added to the emulsion to adjust isotonicity. In the most preferred emulsions of this invention, the PFC ether hydride is present in about 40% by volume, the lecithin in about 2.0 w/v%, and the safflower oil, if present, in about 2.0 v/v% of the emulsion.

As described above, the emulsions of this invention are useful as contrast media by various biological imaging modalities, e.g., nuclear magnetic resonance, $^{19}$F-magnetic resonance imaging, ultrasound, x-ray, and computed tomography. In addition, the emulsions are useful as contrast agents and for direct imaging in $^{19}$F-MRI. When used as contrast media, the emulsions of the invention may be administered, for example, by bolus, orally, subcutaneously, intraperitoneally, intrathecally, or other medically approved method of administration, e.g., catheterization, to the degree necessary such that the emulsions are capable of producing clear concise shadows of the desired part or parts of the anatomy.

The emulsions of this invention may also be used as artificial bloods and infused intravenously to animals or humans suffering from blood loss or oxygen depleted blood. Besides the utility of such artificial bloods for animals and humans, these emulsions can be used as a perfusate for the preservation of internal organs, such as with organ transplants, for extended periods outside the body. Publications demonstrating the usefulness of highly fluorinated organic compound-containing emulsions to preserve organs outside the body of a human or an animal include Kawamura et al., "A New Simple Two Layer (Euro-Collins' Solution/Perfluorochemical) Cold Storage Method For Pancreas Preservation", *Transplantation Proc.*, 21, pp. 1376–77 (1989); Segel and Ensunsa, "Albumin Improves Stability And Longevity Of Perfluorochemical-Perfused Hearts", *Am. J. Physiol.*, 254, pp. H1105–12 (1988); Segel et al., "Prolonged Support Of Working Rabbit Hearts Using Flusol-43 Or Erythrocyte Media", *Am. J. Physiol.*, 252, pp. H349–59 (1987); Segel and Rendig, "Isolated Working Rat Heart Perfusion With Perfluorochemical Emulsion Fluosol-43", *Am. J. Physiol.*, 242, pp. H485–89 (1982). The emulsions of this invention are similarly useful.

The ability of PFC ether hydrides to carry oxygen make them useful when dispersed as emulsions to enhance cancer radiation treatment and chemotherapy, in coronary balloon angioplasty, and in the treatment of heart attack, stroke and other vascular obstructions. Publications demonstrating the usefulness of such emulsions to enhance cancer radiation treatment and chemotherapy include Teicher and Rose, "Oxygen-Carrying Perfluorochemical Emulsion As An Adjuvant To Radiation Therapy In Mice", *Cancer Res.*, 44, pp. 4285–88 (1984); Teicher and Rose, "Effects Of Dose And Scheduling On Growth Delay Of The Lewis Lung Carcinoma Produced By The Perfluorochemical Emulsion, Fluosol-DA", *Int. J. Radiation Oncology Biol Phys.*, 12, pp. 1311–13 (1986); Rockwell et al., "Reactions of Tumors And Normal Tissues In Mice To Irradiation In The Presence And Absence Of A Perfluorochemical Emulsion", *Int. J. Radiation Oncology Biol. Phys.*, 12, pp. 1315–18 (1986); Teicher and Rose, "Perfluorochemical Emulsions Can Increase Tumor Radiosensitivity", *Science*, 223, pp. 934–36 (1984); Teicher et al., "Effect Of Various Oxygenation Conditions And Fluosol-DA On Cytotoxicity And Antitumor Activity Of Bleomycin In Mice", *J. Natl. Cancer Inst.*, 80, pp. 599–603 (1988). The emulsions of this invention are similarly useful.

Publications demonstrating the usefulness of highly fluorinated organic compound-containing emulsions to minimize the adverse effects of coronary balloon angioplasty include Virmani et al., "Myocardial Protection By Perfluorochemical Infusion During Transient Ischemia Produced By Balloon Coronary Occlusion", *Am. Heart J.*, 116, pp. 421–31 (1988); Jaffe et al., "Preservation Of Left Ventricular Ejection Fraction During Percutaneous Transluminal Coronary Angioplasty By Distal Transcatheter Coronary Perfusion Of Oxygenated Fluosol DA 20%", *Am. Heart J.*, 115, pp. 1156–64 (1988); Cleman et al., "Prevention Of Ischemia During Percutaneous Transluminal Coronary Angioplasty By Transcatheter Infusion Of Oxygenated Fluosol DA 20%" *Circulation*, 74, pp. 555–62 (1986); Anderson et al., "Distal Coronary Artery Perfusion During Percutaneous Transluminal Coronary Angioplasty", *Am. Heart J.*, 110 pp. 720–26 (1984). The emulsions of this invention are similarly useful.

Publications demonstrating the usefulness of highly fluorinated organic compound-containing emulsions for treating heart attack, stroke and vascular occlusions include Peerless et al, "Modification Of Cerebral Ischemia With Fluosol", *Stroke*, 16, pp. 38–43 (1985); Osterholm et al., "Severe Perfusion With An Oxygenated Fluorocarbon Emulsion", *Neurosurg.*, 13, pp. 381–87 (1983); Peerless et al., "Protective Effect Of Fluosol-DA In Acute Cerebral Ischemia", *Stroke,* 12, pp. 558–63 (1981); Forman et al., "Reduction Of Infarct Size With Intracoronary Perfluorochemical In A Canine Preparation Of Reperfusion", *Circulation,* 71, pp. 1060–68 (1985). The emulsions of this invention are similarly useful.

The emulsions of this invention may be prepared by conventional mixing of the perfluoroalkyl ether hydrides fluorinated components (discontinuous phase) with an aqueous (continuous) phase and a surfactant. Alternatively, the emulsions of this invention may be prepared by mixing an aqueous phase with any suitable surfactant, and optionally, osmotic agents, buffering agents, electrolytes if desired, other emulsifying agents, additional anti-oxidants, and the like into an aqueous dispersion. The perfluoroalkyl ether hydrides may then be mixed into the aqueous dispersion so as to provide an emulsion of this invention.

The emulsions of this invention may also be prepared by pre-mixing an aqueous dispersion with any suitable surfactant(s) and, optionally, other conventional components of artificial bloods, e.g., osmotic agents and the like. The oil, if present, may then be mixed into the above-described aqueous dispersion at a predetermined rate. The perfluoroalkyl ether hydrides may then be mixed in at a predetermined rate so as to provide an emulsion of this invention.

The resulting emulsion is sterilized, preferably at temperatures in excess of 115° C., more preferably at about 121° C., packaged and otherwise processed for storage and use.

The mixing, pre-mixing if desirable, and emulsification of the components may be done using any of the conventional mixers, homogenizers, and emulsifiers. For example, one may employ Fisher brand touch mixers and microfluidizers or Gaulin homogenizers. In preparing the emulsions of this invention, we prefer to use an inert atmosphere (e.g., $N_2$) to prevent degradation of the surfactant and fatty oils, if present, and to use temperatures between about 45° C. and 55° C.

This invention is further illustrated by the following examples, but the particular materials and amounts thereof recited in these examples, as well as other conditions and details, should not be construed to unduly limit this invention.

I. PREPARATION OF PFC ETHER HYDRIDES

Example 1

Preparation of $C_8F_{17}$-O-$C_2F_4$H from $C_8F_{17}$-O-$C_2F_4CO_2CH_3$

The organic starting material, $C_8H_{17}$-O-$C_2H_4CO_2CH_3$, was prepared by base-catalyzed Michael addition of n-octanol to acrylonitrile, followed by acid-catalyzed methanolysis. The methyl ester was directly fluorinated with $F_2$ to produce the fluorinated ester, $C_8F_{17}$-O-$C_2F_2CO_2CF_3$. This fluorination was carried out in a 2-liter, jacketed reactor vessel of Monel™ metal equipped with a magnetic drive agitator, gas feed line, organic reactant feed line, and a reflux condenser. The gas feed line was 0.3 cm diameter tube reaching to a point below the bottom impeller of the agitator. The feed line was a 0.15 cm diameter tube connected to a syringe pump. The reflux condenser consisted of about 6 meters of two coiled concentric tubes, the inner tube having a 1.27 cm diameter and the outer tube having a 2.54 cm diameter. Gases from the reactor were cooled in the inner tube by refrigerant, ethylene glycol-water, flowing in the annulus between the two tubes. The reactor was charged with about 1.8 liters of Freon™ 113 chlorofluorocarbon and purged with 650 ml/min of nitrogen for 20 minutes. The gas stream was then changed to a mixture of 310 ml/min fluorine and 1100 ml/min nitrogen. After about 12 minutes, 100 g of $C_8H_{17}$-O-$C_2H_4$-$CO_2CH_3$, diluted to 260 ml with Freon™ 113 chlorofluorocarbon, was fed to the reactor at a rate of 13 ml/hr (5 g/hr feed rate). The reactor contents were maintained at about 16°–18° C. throughout the fluorination. The condenser temperature was about –22° C. The fluorine flow was continued for ten minutes after complete addition of the organic feed. The reactor was then purged with nitrogen for one hour. The Freon™ 113 solution of the crude perfluorinated ester was treated with 150 ml of 14% $BF_3$ in methanol and agitated vigorously for 24 hrs. The mixture was washed with water, dried over $MgSO_4$ and distilled (b.p. 40° C./0.2 torr) to yield $C_8F_{17}$-O-$C_2F_4$-$CO_2CH_3$ (47% yield). For purposes of decarboxylation, 39 g of 85% KOH was dissolved in approximately 300 ml of ethylene glycol and the above-described fluorinated methyl ester was added dropwise with stirring to the KOH solution at room temperature. Upon complete addition, the reaction mixture had a pH of 8 to 9. The mixture was heated slowly with stirring and the product of decarboxylation, $C_8F_{17}$-O-$C_2F_4$H, was distilled along with methanol from saponification of the methyl ester, water from the KOH and a small amount of ethylene glycol. When the reaction mixture temperature reached 170° C., the heating was stopped. The lower fluorochemical phase of the distillate was separated, washed with water, dried and distilled through a three-plate Snyder column. The main fraction, boiling at 146°–150° C., yielded 122 g of product. Gas chromatography and mass spectrometry (GC/MS) of a sample of the product showed the sample to be 94% pure and confirmed the structure as $C_8F_{17}$-O-$C_2F_4$H.

Example 2

Preparation of $C_8F_{17}$-O-$C_2F_4$H from $C_8F_{17}$-O-$C_2F_4CO_2$H $C_8H_{17}$-O-$C_2H_4CO_2CH_3$ was prepared by base-catalyzed Michael addition of n-octanol to acrylonitrile, followed by acid-catalyzed methanolysis. This carboxylic acid ester was directly fluorinated by essentially the same fluorination procedure described in Example 1 to produce the corresponding ether acid, $C_8F_{17}$-O-$C_2F_4$COOH upon hydrolysis.

A solution of 116 g of 85% KOH in 800 ml of ethylene glycol was prepared in a 3 L round-bottom flask. 1000 g of the $C_8F_{17}OC_2F_4$-$CO_2$H was added dropwise to the stirred KOH solution. Upon complete addition, an additional 10 g of KOH was added and the mixture heated. The fluorochemical product of decarboxylation was distilled together with a small amount of water from the neutralization of the acid. The lower fluorochemical phase of the distillate was separated, washed with salt water, dried over $Na_2SO_4$ and distilled as in Example 1 to yield 817 g of $C_8F_{17}$-O-$C_2F_4$H.

Example 3

Preparation of $C_7F_{15}$-O-$C_2F_4$H from $C_7F_{15}$-O-$C_2F_4CO_2CH_3$ $C_7H_{15}$-O-$C_2H_4CO_2CH_3$ was prepared by base-catalyzed Michael addition of n-heptanol to acrylonitrile, followed by acid-catalyzed methanolysis. 550 g of the corresponding methyl ester, $C_7F_{15}$-O-$C_2F_4$COOCH$_3$, (prepared by essentially the same fluorination and methanolysis procedures of Example 1 ), was added dropwise to a solution of 166.6 g of KOH in approximately 880 ml of ethylene glycol. The fluorochemical product was recovered essentially as in Example 1 to yield 440 g which was distilled through a six-plate Snyder column and the fraction boiling from 130° to 131° C. was collected (340 g). This fraction was combined with 8.5 g of $KMnO_4$ and approximately 350 g of acetone and heated to reflux. After four hours, an additional 5 g of $KMnO_4$ was added and the resulting mixture was heated for an additional 3 hours. The mixture was filtered, the filter cake washed with acetone, and water was added to the filtrate causing a lower fluorochemical phase to form which was then washed with water, followed by conc. $H_2SO_4$, again with water, and then filtered through silica. $^1$H-NMR and $^{19}$F-NMR confirmed the reaction product to have the desired structure, $C_7F_{15}$-O-$C_2F_2$H. Gas-liquid chromatography of a sample showed it to be 98.7% pure.

Example 4

Preparation of $C_6F_{13}$-O-$C_2F_4$-O-$CF_2$H from $C_6F_{13}$-O-$C_2F_4$-$OCF_2CO_2CH_3$ The starting material, $C_6H_{13}$-O-$C_2H_4$-O-$C_2H_4$-O-$COCH_3$ was prepared by acetylation of hexyloxyethoxy ethanol with acetyl chloride. The acetate was then converted to $C_6F_{13}$-O-$C_2F_4$-$OCF_2CO_2CH_3$ by essentially the same fluorination and methanolysis procedures of Example 1. 548 g of this fluorochemical was combined with 144.2 g of KOH in 600 g of ethylene glycol. The resulting mixture was heated, distilled and the product, $C_6F_{13}$-O-$C_2F_4$-$OCF_2$H, was recovered as in Example 1. Total yield was 433 g. The product was again distilled (b.p. 131° C.) through a 12-inch (30.5 cm) perforated-plate column at atmospheric pressure. The structure of the product was confirmed by $^1$H- and $^{19}$F-NMR as $C_6F_{13}$-O-$C_2F_4$-$OCF_2$H. GC/MS revealed a sample of it to be 99.6% pure.

Example 5

Preparation of $C_8F_{17}$-O-$CF_2$H from $C_8F_{17}$-O-$CF_2$-$CO_2CH_3$ $C_8H_{17}$-O-$C_2H_4$-O-(CO)$CF_3$ was prepared by acetylation of octyloxyethanol with trifluoroacetic anhydride. 100 g of the trifluoroacetate was directly fluorinated by essentially the same fluorination procedures of Example 1 and the fluorination product was quenched with a solution of $BF_3$ in methanol to yield crude $C_8F_{17}$-O-$CF_2$-$CO_2CH_3$, which was further purified by distillation, b.p. 92°–97° C. @20 torr.

A 58 g sample of the latter methyl ester was decarboxylated using 10.8 grams of KOH in ethylene glycol and the product, $C_8F_{17}$-O-$CF_2$H, was recovered as in Example 1. The structure of the product was confirmed by $^{19}$F-NMR. GLC revealed the product to be 99.6% pure, b.p. 134°–136° C.

Example 6

Preparation of $C_4F_9$-O-$(CF_2)_5$H from $C_4F_9$-O$(CF_2)_5$-$CO_2$H 118.2 g (1.0 mol) hexane-1,6-diol, 4.4 g Adogen™ 464 quaternary ammonium salt, 80.0 g (2.0 mol) NaOH, and 250 ml tetrahydrofuran was stirred at reflux. 80 ml $H_2O$ was added to get better mixing. After 20 min more, 137 g (1.0 mol) butyl bromide was added over 0.5 hr, and stirred overnight at reflux. The reaction mixture was quenched in 1 L $H_2O$, and the upper layer was combined with an ether extract of the lower layer, dried over $MgSO_4$, and stripped on a rotary evaporator. Treating the resulting stripped layer (151 g) in 100 ml $CHCl_3$ with 150 ml acetyl chloride added dropwise and subsequently heating at reflux 4 hr and solvent removal gave 225.4 g of liquid. Distillation of the liquid gave 176.0 g (b.p. 100°–104° C./0.9 torr) of distillate. GLC indicated 56% of it to be the desired 6-butoxyhexyl acetate, accompanied by hexanediol diacetate and dibutoxyhexane. 100 g of this mixture was fluorinated essentially as in Example 1. Treatment of the resulting fluorinated product with 30 ml of a 10 weight percent solution of $H_2SO_4$ in $H_2O$ and shaking at room temperature for 2 hours, filtration of solid fluorinated adipic acid, separation of the F-113 layer, drying over $MgSO_4$, and distillation produced a main cut of 73.4 g, b.p. 116° C./20 torr, 96% pure $C_4F_9$-O-$(CF_2)_5$COOH. The latter was added to a solution of 10.0 g (0.25 mol) NaOH and 100 ml ethylene glycol and the mixture was heated to 120° C., with $C_4F_9$-O$(CF_2)_6$-O-$C_4F_9$ impurity from fluorination collecting in the Dean-Stark trap. On continued heating, gas evolution began and a liquid, $C_4F_9$-O$(CF_2)_5$H, (44.6 g) collected in the trap, ending by 170° C. The collected liquid was dried over silica gel and distilled on a 4-inch (10.2 cm) Vigreux column to 38.8 g, b.p. 131° C. F-NMR confirmed structure, in high purity, to be $C_4F_9$-O-$(CF_2)_5$H.

Example 7

Preparation of $C_5F_{11}$-O-$(CF_2)_5$H from $C_5F_{11}$-O-$(CF_2)_5$COOH

In a similar fashion to Example 6, hexanediol was alkylated with n-pentyl bromide, the product was acetylated, and the crude acetate, $C_5H_{11}$-O-$(CH_2)_6OC(O)CH_3$, was distilled (b.p. 125° C./3 torr) and the distillate was fluorinated essentially by the fluorination procedure of Example 1. The fluorinated ester was hydrolyzed to the corresponding acid. Decarboxylation of the fluorinated acid, $C_5F_{11}O(CF_2)_5$COOH with NaOH gave 829 g of product. The product was washed with water, dried over MgSO4, and distilled to yield 555 g of $C_5F_{11}$-O-$(CF_2)_5$H, b.p. 145°–149° C.

Example 8

Preparation of $C_4F_9$-O-$CF_2C(CF_3)_2CF_2$H from $C_4F_9$-O-$CF_2C(CF_3)_2CF_2$Cl The alkylation of 2, 2-dimethyl-1, 3-propanediol with n-butyl bromide carried out essentially as in Example 8 gave the crude mono-alkylated product which was treated with $SOCl_2$ to give $C_4H_9$-O-$CH_2C(CH_3)_2CH_2$Cl, b.p. 80°–90° C./20-30 torr. This compound was then fluorinated as in Example 1 to give $C_4F_9$-O-$CF_2C(CF_3)_2CF_2$Cl. 20.0 g of the latter chloride was mixed with 5.3 g water-wet Raney Ni and 50 ml of $NH_3$-saturated methanol. The mixture was left shaking on a Parr hydrogenation apparatus for 3 days at about 25° C., with most of the 21 kPa (3 psig) hydrogen pressure drop occurring in the first day. The product was recovered by filtration and quenched in water, yielding 7.9 g with some mechanical loss. $^{19}$F-NMR confirmed the product to be $C_4F_9$-O-$CF_2C(CF_3)_2CF_2$H. A scaleup to 100 g gave 47 g, distilled to b.p. 135° C.

Example 9

Preparation of $H(CF_2)_4-O-(CF_2)_2H$ from $Cl(CF_2)_4-O-(CF_2)_4Cl$

Cl-$(CF_2)_4$-O-$(CF_2)_4$Cl was fluorinated as in Example 1 to provide Cl$(CF_2)_4$-O-$(CF_2)_4$Cl. A mixture of 30.3 g Cl$(CF_2)_4$-O-$(CF_2)_4$Cl, 11.3 g fresh water-wet Raney Ni, and 200 ml methanol was purged for several minutes with $NH_3$ and pressurized with 310 kPa (45 psig) hydrogen on a Parr hydrogenation apparatus at about 25° C. After 17 hr, pressure had dropped to 255 kPa (37 psig) and the mixture had become acidic, with glass etching noted. More ammonia was added and the reduction was continued, dropping another 62 kPa (9 psig). The reaction product was filtered and quenched in water to give 15.4 g of lower phase, 68% pure product confirmed by GLC to be J$(CF_2)_4$-O-$(CF_2)_4$H. Distillation yielded 27.0 g, b.p. 121°–124° C., 87 % pure.

Example 10

Preparation of $H(CF_2)_4-O-(CF_2)_4H$ and $Cl(CF_2)_4-O-(CF_2)_4H$ from $Cl(CF_2)_4-O-(CF_2)_4Cl$ A mixture of 50.0 g Cl$(CF_2)_4$-O-$(CF_2)_4$Cl and 30 g Zn in butanol was stirred at 110° C. for 2 days. GLC of a sample of the resulting reaction product indicated partial conversion. 21 g more Zn was added and the mixture was heated one more day. Filtration and quenching of the resulting material in water gave 27.0 g of a colorless liquid. The product was 35% of H$(CF_2)_4$-O-$(CF_2)_4$H, 42 % mono hydride, and 16% unreduced dichloride.

Example 11

Preparation of $C_6F_{13}-O-CF_2CF_2H$ from $C_6F_{13}-O-C_2F_4CO_2H$

The starting material, $C_6H_{13}$-O-$C_2H_4$-$CO_2CH_3$ was prepared by the Michael addition of hexanol to acrylonitrile followed by acid-catalyzed esterification with methanol, The resulting ester was then fluorinated and hydrolyzed to give the $C_6F_{13}$-O-$C_2F_4CO_2H$.

500 g of the acid, $C_6F_{13}$-O-$C_2F_4CO_2H$, was added slowly to a solution of 68.7 g KOH in 700 g ethylene glycol. At the end of the addition, an additional 5 g of KOH was added to the homogeneous solution to bring the pH to 9, The decarboxylation was carried out as in Example 1 and subsequently distilled, producing 327 g of product, b.p. 104°–107° C. The product was treated with potassium permanganate essentially as in Example 3. GC/MS, $^{19}$F-NMR, $^1$H-NMR and IR confirmed structure of the product as $C_6F_{13}$-O-$CF_2$-$CF_2$H.

Example 12

Preparation of $C_4F_9-O-(CF_2)_4-O-(CF_2)_3H$ from $C_4F_9-O-C_4F_8-O-(CF_2)_3CO_2CH_3$ The starting material, $C_4H_9$-O-$C_4H_8$-O-$(CH_2)_3CH_2OCOCH_3$, was directly fluorinated and methanolysed essentially by the procedures of Example 1 to produce $C_4F_9$-O-$C_4F_8$-O-$(CF_2)_3CO_2CH_3$. 56 g of the latter was added rapidly to a solution of 5.6 g KOH in 250 ml of ethylene glycol. The decarboxylation was carried out and the product phase separated, washed once with brine, and distilled to yield 36.6g of product (b.p. 155°–158° C.) of GLC purity 100%. GC/MS, $^1$H-, and $^{19}$F-NMR analysis confirmed the product to be $C_4F_9$-O-$C_4F_8$-O-$(CF_2)_3$H.

Example 13

Preparation of cyclo-$C_6F_{11}CF_2-O-C_2F_4H$ from cyclo-$C_6F_{11}CF_2-O-C_2F_4C(O)OCH_3$ The starting material, cyclo-$C_6H_{11}CH_2$-O-$C_2H_4C(O)OCH_3$, prepared by the reaction of cyclohexylmethanol with acrylonitrile followed by acid-catalyzed esterification with methanol, was then fluorinated and methanolysed with $BF_3$ in methanol by essentially the procedures of Example 1, to give a 65% yield of cyclo-$C_6F_{11}CF_2OC_2F_4CO_2CH_3$.

224 g of the latter fluorinated ester was added to a solution of 28.2 g of 85% KOH and 466 g ethylene glycol held at 60° C. The resulting mixture was then heated to 100° C. and its pH adjusted to a pH greater than 7 by the addition of 5 g of 45 wt % aqueous KOH. Decarboxylation was carried out by distillation of the resulting mixture. The lower fluorochemical phase of the resulting distillate was separated therefrom, washed with an equal volume of water, and distilled at 123°–126° C. to give 155 g of a product (99.7% purity). The product was treated with $KMnO_4$ in acetone to give cyclo-$C_6F_{11}CF_2$-O-$C_2F_4$H.

Example 14

Preparation of $C_4F_9-O-C_2F_4-O-C_3F_6H$ from $C_4F_9-O-C_2F_4-O-C_3F_6C(O)OCH_3$ $C_4H_9$-O-$C_2H_4$-O-$C_4H_8OCOCH_3$ was fluorinated and methanolysed by essentially the procedure of Example 1. The resulting product, $C_4F_9$-O-$C_2F_4$-O-$C_3F_6C(O)OCH_3$, in the amount of 419 g was rapidly added dropwise to a mixture of 49.4 g KOH in 800 g ethylene glycol. The resulting mixture was then heated slowly to a final flask temperature of 190° C. During such heating, methanol from the saponification of the ester, water, and $C_4F_9$-O-$C_2F_4$-O-$C_3F_6$H distilled from the reaction mixture. Water was added to the distillate and the lower, fluorochemical phase (355 g) was separated and distilled (b.p. 120°–122° C.) to provide 308 g $C_4F_9$-O-$C_2F_4OC_3F_6$H (82% yield).

Example 15

Preparation of $C_6F_{13}-O-C_4F_8-H$ from $C_6F_{13}-O-C_4F_8-CO_2CH_3$

The starting material, $C_6H_{13}$-O-$C_5H_{10}$-OC(O)$CH_3$, was prepared by monoalkylation of 1,5-pentanediol with hexyl bromide, followed by acetylation with acetyl chloride. This compound was fluorinated and methanolysed by essentially the procedure of Example 1, to give $C_6F_{13}$-O-$C_4F_8$-$CO_2CH_3$, b.p. 100° C. @ 13 tor. This ester was decarboxylated by heating a solution of 200 grams of ester in 250 ml of ethylene glycol with 30 g of KOH until the hydride product distilled. This liquid was washed with water, dried over $MgSO_4$ to give 128 g of $C_6F_{13}$-O-$C_4F_8$-H of 82% purity. This was further purified by distillation using a twelve-plate packed glass column, b.p. 146° C. The structure was confirmed by $^{19}$F-NMR.

Example 16

Preparation of $C_6F_{13}-O-C_3F_6-H$ from $C_6F_{13}-O-C_3F_6-CO_2K$

The starting material, $C_6H_{13}$-O-$C_4H_8$-OC(O)$CH_3$, was prepared by monoalkylation of 1,4-butanediol with hexyl bromide, followed by acetylation with acetic anhydride.

This compound was fluorinated and methanolysed by essentially the procedure of Example 1, to give $C_6F_{13}$-O-$C_3F_6CO_2CH_3$. The methyl ester was saponified using excess KOH, and then dried in a vacuum oven to yield the potassium salt. 575 g of the salt was heated with stirring in 250 ml of ethylene glycol and the product hydride recovered from the distillate, b.p. 129° C. The structure was confirmed by $^{19}$F-NMR.

Example 17

Preparation of $C_5F_{11}$-O-$C_4F_8$-H from $C_6F_{11}$-O-$C_4F_8$-$CO_2$-Na

The starting material, $C_5H_{11}$-O-$C_5H_{10}$-O-C(O)$CH_3$ was prepared by monoalkylation of 1,5-pentanediol with pentyl bromide, followed by acetylation with acetyl chloride. This compound was fluorinated and methanolysed by essentially the procedure of Example 1 to give $C_5F_{11}$-O-$C_4F_8$-$CO_2CH_3$. The methyl ester was saponified using excess NaOH, and decarboxylated and distilled essentially as in Example 16. Distillation through a twelve-plate packed glass column gave pure $C_5F_{11}$-O-$C_4F_8$-H b.p. 125° C. The structure was confirmed by $^{19}$F-NMR.

Example 18

Preparation of $C_8F_{17}OCF_2OC_3F_6H$ from $C_8F_{17}OCF_2OC_3F_6CO_2CH_3$

The precursor, $C_8H_{17}OCH_2OC_4H_8OH$ was prepared by monoalkylation of butane diol with octyl chloromethyl ether. The precursor was first acetylated with acetyl chloride in methylene chloride containing triethylamine and then fluorinated.

A portion of the crude perfluorinated products was methanolysed essentially as in Example 1 to yield $C_8F_{17}OCF_2OC_3F_6CO_2CH_3$, having a boiling range 124°–130° C. at 25 torr. The latter methyl ester was then decarboxylated using the procedure of Example 1 to yield $C_8F_{17}OCF_2OC_3F_6H$, having a boiling range of 178°–183° C.; the structures of this hydride and the precursor fluorinated ester were confirmed by $^{19}$F-NMR.

Example 19

Preparation of

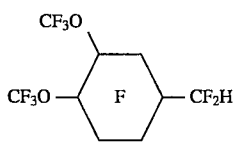

The starting material, methyl 2-(3,4-dimethoxyphenyl)acetate was fluorinated essentially as in Example 1 to yield perfluoro-2-(3,4-dimethoxycyclohexyl)acetic acid after hydrolysis. This was then decarboxylated as described in Example 1 to the perfluorinated ether hydride.

Example 20

Preparation of

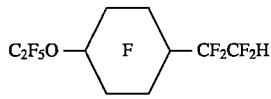

The starting material, methyl 3-(4-ethoxyphenyl)-trans-2-propenoate was prepared by condensation of 4-ethoxybenzaldehyde with malonic acid, followed by esterification. This methyl ester was fluorinated, methanolized and decarboxylated essentially as in Example 1 to produce the perfluorinated ether hydride.

Example 21

Preparation of

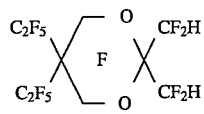

The starting material was prepared by condensation of 2,2-diethyl propane diol with dimethyl 3-oxoglutarate. This dimethyl ester was fluorinated, methanolyzed to the diester, and decarboxylated as in Example 1 to produce the perfluorinated ether dihydride.

Example 22

Preparation of

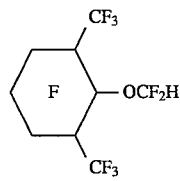

The starting material was prepared by reaction of 2,6-dimethylphenol with ethylene carbonate and subsequent acetylation with acetyl chloride. This acetate was fluorinated, methanolyzed and decarboxylated as in Example 1 to produce the perfluorinated ether hydride, b.p. 132° C.

Example 23

Preparation of

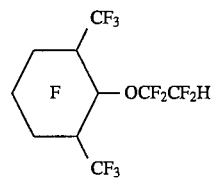

The starting material was prepared by the treatment of 2-(2,6-dimethylphenyloxy)ethanol with thionyl chloride. This was fluorinated as in Example 1 followed by Raney Ni reduction of the chloride as described in Example 8 to produce the perfluorinated ether hydride, distilling at 145°–150° C.

Example 24

Preparation of

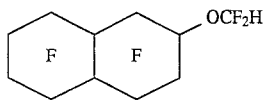

The starting material was prepared from the addition of β-napthol to ethylene carbonate, followed by acetylation with acetyl chloride. This acetate was fluorinated, methanolyzed and decarboxylated as in Example 1 to produce the perfluorinated ether hydride, b.p. 171° C.

Example 25

Preparation of $C_7F_{15}OCHFCF_3$ from $C_7H_{15}OCH(CH_3)CO_2CH_3$

The starting material was prepared by the addition of 2-chloropropionic acid to n-heptanol and aq. sodium hydride, followed by esterification to the methyl ester. This ester was fluorinated and decarboxylated as in Example 1 to produce the perfluorinated ether hydride, b.p. 130° C.

Example 26

Preparation of $C_4F_9OCHFOC_4F_9$ from $(C_4H_9O)_2CHCO_2C_4H_9$

The starting material was prepared by the addition of dichloroacetic acid to sodium butoxide in n-butanol and subsequent acidification in butanol. This ester was fluorinated, methanolyzed and decarboxylated as in Example 1 to produce the perfluorinated ether hydride.

Example 27

Preparation of $C_7F_{15}OCHFC_2F_5$ from $C_7H_{15}OCH(C_2H_5)CO_2CH_3$

The starting material was prepared by the addition of 2-bromobutyric acid to n-heptanol and sodium hydroxide, followed by esterification with methanolic HCl. This ester was fluorinated, methanolyzed and decarboxylated as in Example 1 to produce the perfluorinated ether hydride.

Example 28

Preparation of $C_6F_{11}OCF_2C(CF_3)_2CF_2H$ from $C_5H_{11}OCH_2C(CH_3)_2CH_2Cl$ The starting material was prepared as described U.S. Ser. No 08/246962 filed May 20, 1994 (3M). The ether chloride was fluorinated as in Example 1 followed by Raney Ni reduction of the chloride as described in Example 8 to produce the perfluorinated ether hydride b.p. 148° C.

Example 29

Preparation of $(C_4F_9O)_2CFCF_2H$ from $(C_4H_9O)_2CHCH_2Cl$

The starting material was prepared by the addition of n-butanol to 2-chloroacetaldehyde and was fluorinated as in Example 1 followed by Raney Ni reduction of the chloride as described in Example 8 to produce the perfluorinated ether hydride.

Example 30

Preparation of $CF_3O(CF_2)_9H$ from $CH_3O(CH_2)_{10}OAc$

The starting material was prepared by monoalkylation of 1,10-decanediol with dimethyl sulfate, followed by acetylation with acetyl chloride. This acetate was fluorinated, hydrolyzed and decarboxylated as in Example 1 to produce the perfluorinated ether hydride.

Example 31

Preparation of $C_9F_{19}OCF_2H$ from $C_9H_{19}OC_2H_4OAc$

The starting material was prepared by monoalkylation of ethylene glycol with n-nonyl bromide, followed by acetylation with acetyl chloride. This acetate was fluorinated, hydrolyzed and decarboxylated as in Example 1 to produce the perfluorinated ether hydride, distilling at 153°–155° C.

Example 32

Preparation of $(iso-C_3F_7)_2CFOC_2F_4H$ from $(iso-C_3H_7)_2CHOC_2H_4CO_2CH_3$ The starting material was prepared by Michael addition of 2,4-dimethyl-3-pentanol to acrylonitrile followed by methanolysis to the methyl ester. This ester was fluorinated, hydrolyzed and decarboxylated as in Example 1 to produce the perfluorinated ether hydride.

Example 33

Preparation of $C_7F_{15}OCHFCF_3$ from $C_7H_{15}OCH(CH_3)CO_2CH_3$

The starting material was prepared by addition of 2-chloropropionic acid to n-heptanol and sodium hydroxide, followed by esterification with methanolic HCl. This was fluorinated as in Example 1, then treated with pyridine to produce $C_7F_{15}OCF(CF_3)CO_2F$ with loss of $COF_2$. This acid fluoride was decarboxylated as in Example 1 by addition to KOH in ethylene glycol and subsequent heating. The product was formed at a pot temperature of 126° C. and was collected by distillation b.p. 130° C.

Example 34

Preparation of

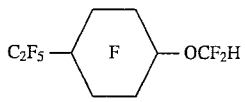

The starting material was prepared by the alkylation of 4-ethylphenol with methyl chloroacetate. This ester was fluorinated, hydrolyzed and decarboxylated as in Example 1 to produce the perfluorinated ether hydride, b.p. 131° C.

Example 35

Preparation of

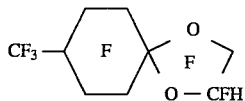

The starting material was prepared by the addition of glycerol to 4-methylcyclohexanone, followed by acetylation with acetyl chloride. This acetate was fluorinated, hydrolyzed and decarboxylated as in Example 1 to produce the perfluorinated ether hydride, b.p. 138° C.

II. PREPARATION OF THE EMULSIONS AND THEIR CLEARANCE PROPERTIES

Emulsions were prepared using PFC ether hydrides (PFEH) above identified. According to this general procedure, a crude emulsion of 2 w/v% egg yolk lecithin, 2 v/v% safflower oil, 40 v/v% PFEH and water under an inert atmosphere ($N_2$) was prepared by mixing at high speed in a Waring blender for about two minutes. The crude emulsion was transferred to a reservoir, again under an inert atmosphere, which fed a MICROFLUIDIZER™ Model #110 homogenization apparatus. This crude emulsion was then cycled through the homogenizer at a pressure of about 8,000 psi and at a flow rate of 350 ml/min, using 60 psig air pressure to drive the pump piston, for a total of about 15 minutes. The temperature was maintained below 50° C. throughout, and the pH was controlled between about 7.5 and 8.5. After preparing the emulsions of 2 w/v% lecithin, 2 v/v% oil and 40 v/v% PFEH, each was loaded under nitrogen into a 100 ml type I glass bottle and the bottle was sealed with Teflon™-lined butyl rubber septums and aluminum closures. The bottled emulsions were heat-sterilized by heating them to about 121° C. for about 15 minutes, with moist steam heat in a rotating sterilizer.

To compare the physiological characteristics of the compounds prepared as emulsions, clearances of the PFEH in them from the organs of rats over a period up to sixty days, or longer, post-infusion was assessed. As developed above, physiologically useful emulsion must persist for a sufficiently long time in the blood stream to deliver useful quantities of oxygen. However, the fluorochemical must also be eliminated rapidly enough from the body to avoid retention in body parts and/or toxicity. Thus, clearance of the PFEH contained in various emulsions from the organs was assayed as follows. Sprague-Dawley rats were infused with each of the emulsions (10cc/kg per rat). Rats were then sacrificed at each of several time points post infusion. The amount of fluorochemical was assayed in the organs by grinding the tissue in a Tissuemizer™, extracting with carbon tetrachloride containing 0.1–1% n-octane or n-heptane as internal standards, and analyzing the organ extract by gas chromatography. The data are tabulated in the following Table as the percent dose present in the liver over a period of days, for example, "2-16-30" under "TIME PTS" means the percent of dose present in the liver as recorded after 2 days, 16 days and 30 days post infusion. The percent of dose equals the percent of the total PFEH amount infused in the rats.

TABLE

| COMPOUND STRUCTURE | MOLECULAR FORMULA | DOSE cc PFEH per Kg | CLEARANCE FROM LIVER | | | |
|---|---|---|---|---|---|---|
| | | | % DOSE | % DOSE | % DOSES | TIME PTS (DAYS) |
| 1 $H-C_2F_4OCF_2C(CF_3)_2CF_2OC_2F_4-H$ | $C_9F_{18}O_2H_2$ | 1 | 0.0 | 0.0 | | 2-16 |
| 2 $H-C_2F_4-O-C_5F_{10}-O-C_2F_4-H$ | $C_9F_{18}O_2H_2$ | 1 | 2.3 | 0.0 | | |
| 3 $H-C_3F_6-O-C_4F_8-O-C_3F_6-H$ | $C_{10}F_{20}O_2H_2$ | 4 | 45.1 | 17.9 | 5.6 | 2-16-30 |
| 4 $(cycC_6F_{11})-CF_2OC_2F_4-H$ | $C_9F_{17}OH$ | 4 | | | | |
| 5 $CF_3O-(cycC_6F_{10})-C_2F_4-H$, para | $C_9F_{17}OH$ | 1 | 0.0 | 0.0 | | 2-16 |
| 6 $(cycC_6F_{11})-C_2F_4OCF_2-H$ | $C_9F_{17}OH$ | 1 | 0.0 | 0.0 | | 2-16 |
| 7 $(cycC_6F_{11})-OC_4F_8-H$ | $C_{10}F_{19}OH$ | 1 | 17.0 | 0.0 | | 2-16 |
| 8 $CF_3(CF_2)_6-O-CF_2CF_2-H$ | $C_9F_{19}OH$ | 4 | 40.9 | 19.4 | 3.6 | 2-16-30 |
| 9 $C_8F_{17}-O-CF_2-H$ | $C_9F_{19}OH$ | 1 | 35.6 | 10.5 | | 2-16 |
| 10 $C_8F_{17}-O-C_2F_4-H$ | $C_{10}F_{21}OH$ | 4 | 44.3 | 42.9 | 41.7 | 2-16-30 |
| 11 $C_6F_{13}-O-C_4F_8-H$ | $C_{10}F_{21}OH$ | 4 | 42.6 | 50.3 | 41.8 | 2-16-30 |
| 12 $C_5F_{11}-O-C_5F_{10}-H$ | $C_{10}F_{21}OH$ | 4 | 47.3 | 47.1 | 39.9 | 2-16-30 |
| 13 $C_6F_{13}-O-C_2F_4-H$ | $C_8F_{17}OH$ | | | | | LETHAL |
| 14 $C_4F_9OCF(CF_3)CF_2O-CFH-CF_3$ | $C_9F_{19}O_2H$ | 4 | | | | |
| 15 $C_4F_9-O-C_2F_4-O-C_3F_6-H$ | $C_9F_{19}O_2H$ | 1 | 48.1 | 42.6 | | 2-16 |
| 16 $H-CF_2O-(C_2F_4O)_3-CF_2-H$ mixture | $C_8F_{18}O_4H_2$ | 0.13 | | | | |
| $H-CF_2O-(C_2F_4O)_4-CF_2-H$ | $C_{10}F_{20}O_5H_2$ | 0.57 | 27.1 | 18.0 | 11.2 | 2-16-30 |
| 17 $H-C_2F_4-O-C_6F_{12}-O-OC_2F_4-H$ | $C_{10}F_{20}O_2H_2$ | 1 | 30.4 | trace | | |
| 18 $C_7F_{15}-O-CFH-CF_3$ | $C_9F_{19}OH$ | 1 | 28.2 | 0.6 | | 2-16 |
| 19 $C_8F_{17}-O-CFH-CF_3$ | $C_{10}F_{21}OH$ | 1 | 43.5 | 26.6 | | 2-16 |

| COMPOUND STRUCTURE | MOLECULAR FORMULA | DOSE cc PFEH per Kg | CLEARANCE FROM LIVER | | | |
|---|---|---|---|---|---|---|
| | | | % DOSE | % DOSE | % DOSES | TIME PTS (DAYS) |
| 20  $C_4F_9-O-CF_2-\underset{\underset{CF_3}{\|}}{\overset{\overset{CF_3}{\|}}{C}}-CF_2-H$ | $C_9F_{19}OH$ | 1 | 25.6 | 0.0 | | 2-16 |
| 21  $C_5F_{11}-O-CF_2-\underset{\underset{CF_3}{\|}}{\overset{\overset{CF_3}{\|}}{C}}-CF_2-H$ | $C_{10}F_{21}OH$ | 1 | 40.2 | 20.6 | | 2-16 |

With reference to the above Table, it will be appreciated that the $C_9$–$C_{10}$ di-omegahydroperfluorocarbon diethers as a group have the exceptional properties of clearance from the essential organs such as the liver very rapidly, even in a matter of days. For example, with reference to compounds 1 and 2 of the Table, the $C_9$ diomegahydroperfluorocarbon diether cleared the liver immediately or only 2.3% was detectable after two days. In the case of the $C_{10}$ di-omegaperfluorocarbon diether, as represented by compound 17 of the Table, 30.4% of the dose was detectable after two days and within 16 days only a trace was found in the liver. The $C_{10}$ di-omegahydroperfluorocarbon diether as represented by compound 3 of the Table, cleared over a period of 30 days from about 45.1% of the dose to about 5.6% of the dose in the liver.

The exceptional clearance characteristics of the cyclo $C_9$–$C_{10}$ ether hydrides are demonstrated by compounds 4–7 of the Table. For example, the $C_{10}$ perfluorocycloalkyl monoether hydride, compound 7 of the Table, completely cleared the liver within 16 days. Remarkably, in the case of the $C_9$ perfluorocycloalkyl monoether hydride or perfluorocycloalkyl-substituted perfluoroalkylene monoether hydride, with reference to compounds 4–6 of the Table, there was no detectable PFC ether hydride in the liver after two days. Thus, as a class, these compounds are excellent examples of the physiologically acceptable emulsions formulated in accordance with the principles of this invention.

The activities of the $C_9$–$C_{10}$ monohydroperfluoroalkyl monoether or diether compounds are represented by the remaining compounds of the Table, for example, compounds 8–16. In the case of a $C_9$ monohydroperfluoroalkyl monoether, compound 9 of the Table, after 16 days, only 10.5% of the dose of the PFC ether hydride remained in the liver. A $C_{10}$ monohydroperfluoroalkyl monoether, as represented by compounds 10–12 of the Table, tends to reside in the liver for a longer period of time in comparison to the $C_9$ PFC ether hydride. In the case of the $C_8$ monohydroperfluoroalkyl monoether, as represented by compound 13 of the Table, this compound was found to be toxic based upon limited experimentation. However, with reference to the mixture of compounds 16 of the Table, a $C_8$ di-omegahydroperfluorocarbon tetraether, even when combined with a $C_{10}$ di-omegahydroperfluorocarbon pentaether, provides a 100% survival of the animal and clearance from the liver takes place about as rapidly as other di-omegahydro PFC ethers. Thus, to the extent present data may exclude a specific PFC ether hydride from the broader class of compounds, it may be acceptable in mixtures with other compounds. Those PFC ether mixtures which are within the scope of this invention are called "physiologically acceptable" so as to exclude inoperative compounds.

As developed above, the hydrogen atom of the PFC ether hydrides may be bonded at the end or omega carbon atom of the carbon chain or it may be bonded at an intermediate atom such as the case with compound 14 of the Table where the hydrogen atom is bonded on a secondary carbon atom adjacent to an ether group. In the case of compound 14 of the Table, clearance from the liver of this $C_9$ monohydroperfluorocarbon monoether was essentially equivalent to other PFC ether hydrides in the group.

While we have hereinbefore described various embodiments of this invention, it should be apparent that other embodiments also exist within the scope of the invention. Therefore, it should be understood that the scope of this invention is to be defined by the claims rather than the specific embodiments which have been presented hereinbefore by way of example.

What is claimed is:

1. A physiologically acceptable aqueous emulsion comprising a saturated $C_8$ to $C_{12}$ perfluorocarbon ether hydride selected from the group consisting of a hydroperfluoroaliphatic ether, a hydroperfluoroaliphatic ether substituted with a perfluoroalicyclic group, and a hydroperfluorocycloaliphatic ether and mixtures thereof, wherein said aliphatic ether has a straight-chain or a branched-chain of carbon atoms, water and a surfactant, wherein the components are contained in the emulsion in amounts for acceptable physiological administration.

2. The emulsion of claim 1 wherein said ether is $C_9$ to $C_{11}$.

3. The emulsion of claim 1 wherein said ether has a boiling point of at least about 120° C.

4. The emulsion of claim 1 wherein said ether is represented by the formula:

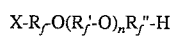

$$X\text{-}R_f\text{-}O(R_f'\text{-}O)_nR_f''\text{-}H$$

wherein:

H is a primary hydrogen atom or a 2° hydrogen atom on a carbon adjacent to an ether oxygen atom;

X is a fluorine atom or a primary hydrogen atom, or a 2° hydrogen atom on a carbon adjacent to an ether oxygen atom;

n is an integer of 0 to 4; and $R_f$, $R_f'$ and $R_f''$ are independently selected from unbranched or branched groups consisting of perfluoroalkylene, perfluorocycloalkylene, or perfluorocycloalkylene containing one or more ether oxygens, and which groups may be substituted with an ether oxygen.

5. The emulsion of claim 1 wherein said ether is a $C_9$–$C_{10}$ dihydroperfluorocarbon ether.

6. The emulsion of claim 5 wherein said ether is selected from the group consisting of $H\text{-}C_3F_6OC_4F_8OC_3F_6\text{-}H$,
$H\text{-}C_2F_4OCF_2C(CF_3)_2CF_2OC_2F_4\text{-}H$,
$H\text{-}C_2F_4\text{-}O\text{-}(CF_2)_5\text{-}O\text{-}C_2F_4\text{-}H$,
$H\text{-}C_2F_4\text{-}O\text{-}(CF_2)_6\text{-}O\text{-}C_2F_4\text{-}H$,
$H\text{-}CF_2O\text{-}(C_2F_4O)_3CF_2\text{-}H$,
$H\text{-}CF_2O\text{-}(C_2F_4O)_4CF_2\text{-}H$ and
$H\text{-}C_2F_4\text{-}O\text{-cyclo-}C_6F_{10}\text{-}O\text{-}C_2F_4\text{-}H$, and mixtures thereof.

7. The emulsion of claim 1 wherein said ether is a $C_9$–$C_{11}$ perfluorocycloalkyl ether hydride or a $C_9$–$C_{11}$ perfluorocycloalkyl-substituted perfluoroalkylene ether hydride.

8. The emulsion of claim 7 wherein said ether is selected from the group consisting of $cyclo\text{-}C_6F_{11}\text{-}CF_2OC_2F_4H$,
$cyclo\text{-}C_6F_{11}\text{-}OC_4F_8H$,
$cyclo\text{-}C_6F_{11}\text{-}C_2F_4OCF_2\text{-}H$,
$p\text{-}CF_3O\text{-}cyclo\text{-}C_6F_{10}\text{-}C_2F_4\text{-}H$,

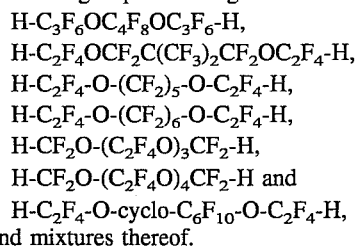

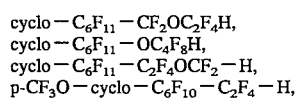

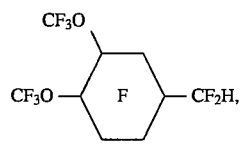

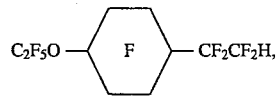

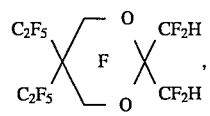

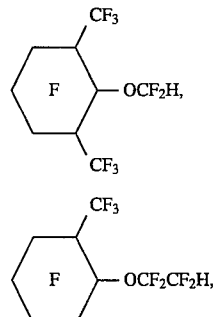

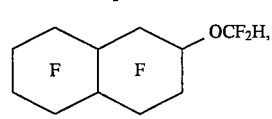

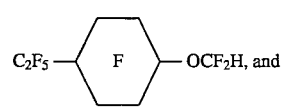

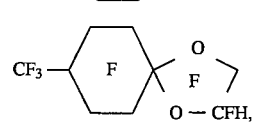

and mixtures thereof.

9. The emulsion of claim 1 wherein said ether is a $C_9$–$C_{10}$ hydroperfluoroalkyl ethers where the hydrogen atom is 1° or is 2° bonded to a carbon atom adjacent to an ether oxygen either bonded to an end carbon or intermediate carbon adjacent to an ether.

10. The emulsion of claim 9 wherein said ether is selected from the group consisting of $C_4F_9OCF(CF_3)CF_2O\text{-}CFH\text{-}CF_3$,
$CF_3(CF_2)_6\text{-}O\text{-}CF_2CF_2\text{-}H$,
$C_8F_{17}OCF_2H$,
$CF_3(CF_2)_5\text{-}O\text{-}(CF_2)_2\text{-}O\text{-}CF_2\text{-}H$,
$C_6F_{13}\text{-}O\text{-}C_4F_8\text{-}H$,
$C_5F_{11}\text{-}O\text{-}C_5F_{10}\text{-}H$,
$C_4F_9\text{-}O\text{-}C_2F_4\text{-}O\text{-}C_3F_6\text{-}H$,

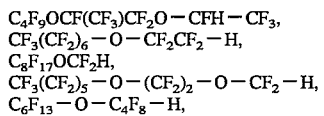
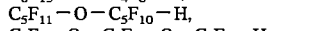
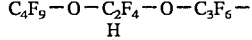
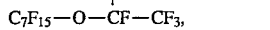
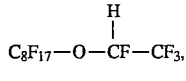
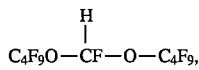
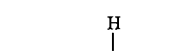
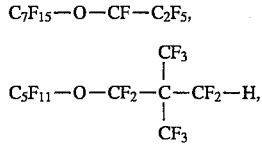
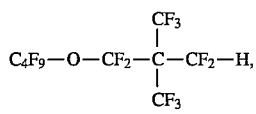
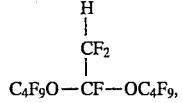

$CF_3O\text{-}C_8F_{16}\text{-}CF_2H$ and
$C_9F_{19}\text{-}O\text{-}CF_2\text{-}H$, and mixtures thereof.

11. The emulsion of claim 1 wherein the surfactant is present in an amount from about 0.5 to about 10% by weight of the emulsion.

12. The emulsion of claim 1 wherein the surfactant is present in an amount from about 1 to about 4% by weight of the emulsion.

13. The emulsion of claim 1 wherein the ether is present in an amount from about 10 to about 75% by volume of the emulsion.

14. The emulsion of claim 13 wherein a surfactant is contained in an amount from about 0.5 to about 10% by weight of the emulsion.

15. The emulsion of claim 1 wherein the said ether is contained in an amount of at least about 40% by volume of the emulsion.

16. The emulsion according to claim 1 wherein the surfactant is lecithin.

17. An emulsion according to claim 16 further comprising a physiologically acceptable oil that is not substantially surface active and not significantly water soluble.

18. The emulsion according to claim 17 wherein the oil is selected from the group consisting of safflower oil and soybean oil.

19. The emulsion according to claim 1 further comprising at least one compound selected from the group consisting of isotonic agents, osmotic pressure controlling agents, serum extending agents and antioxidants.

* * * * *

UNITED STATES PATENT AND TRADEMARK OFFICE
CERTIFICATE OF CORRECTION

PATENT NO. : 5,502,094
DATED : March 26, 1996
INVENTOR(S) : George G. I. Moore, et al.

It is certified that error appears in the above-indentified patent and that said Letters Patent is hereby corrected as shown below:

| | |
|---|---|
| Column 13, line 3, "$(CF_2)_2H$" | should be --$(CF_2)_4H$-- |
| Column 13, line 6, "$Cl\text{-}(CF_2)_4\text{-}O\text{-}(CF_2)_4Cl$" | should be --$Cl\text{-}(CH_2)_4\text{-}O\text{-}(CH_2)_4Cl$-- |
| Column 13, line 17, "$J(CF_2)_4$" | should be --$H(CF_2)_4$-- |
| Column 14, line 51, "tor" | should be --torr-- |
| Column 15, line 16, "$C_6F_{11}$" | should be --$C_5F_{11}$-- |
| Column 17, line 50, "Preparation of $C_6$" | should be --Preparation of $C_5$-- |
| Column 21-22, TABLE, line 5, "25.6" | should be --25.5-- |

Signed and Sealed this

Seventeenth Day of September, 1996

BRUCE LEHMAN

*Attest:*

*Attesting Officer*    *Commissioner of Patents and Trademarks*